US005296350A

United States Patent [19]

Rokita et al.

[11] Patent Number: 5,296,350

[45] Date of Patent: Mar. 22, 1994

[54] ION TRIGGERED ALKYLATION OF BIOLOGICAL TARGETS BY SILYLOXY AROMATIC AGENTS

[75] Inventors: Steven E. Rokita, Port Jefferson; Tianhu Li, Stony Brook, both of N.Y.

[73] Assignee: The Research Foundation of State University of New York, Albany, N.Y.

[21] Appl. No.: 606,463

[22] Filed: Oct. 31, 1990

[51] Int. Cl.[5] ............................................ C12Q 1/68

[52] U.S. Cl. ..................................... 435/6; 436/501; 536/23.1; 935/78

[58] Field of Search .............. 435/6, 91; 536/27, 23.1; 514/44; 935/77, 78; 436/501

[56] References Cited

FOREIGN PATENT DOCUMENTS

WO8502628 6/1985 PCT Int'l Appl. .

OTHER PUBLICATIONS

Landegren et al., "DNA Diagnostics-Molecular Techniques and Automation", Science, 242, 229 (1988).

Miller et al., "Oligonucleotide Inhibitors of Gene Expression in Living cells: New Opportunities in Drug Design", Ann. Reports in Med. Chem., 23, 295 (1988).

Toulme et al., "Antimessenger Oligodeoxyribonucleotides: An Alternative to Antisense RNA for Artificial Regulation of Gene Expression-A Review", *Gene, 72,* 51-58 (1988).

Stein et al., "Oligodeoxyribonculeotides as Inhibitors of Gene Expression: A Review", Cancer Research, 48, 2659-2668 (1988).

Barton, "Metals and DNA: Molecular Left-Handed Complements", Science, 233, 727-734 (1986).

Dervan, "Design of Sequence-Specific DNA-Binding Molecules", Science, 232, 464-471 (1986).

Blake et al., "Hybridization Arrest of Globin Synthesis in Rabbit Reticulocyte Lysates and Cells by Oligodeoxyribonucleoside Methyl-phosphonates", Biochemistry, 24, 6139-6145 (1985).

Agrawal et al., "Oligodeoxynucleoside Phosphoramidates and Phosphorothioates as Inhibitors of Human Immunodeficiency Virus", Proc. Nat'l, Acad. Sci. USA, 85, 7079-7083 (1988).

Inverson et al., "Nonenzymatic Sequence-Specific cleavage of Single-Stranded DNA to Nucleotide Resolution, DNA Methyl Thiolether Probes", *J. Am. Chem. Soc., 109,* 1241-1243 (1987).

Maher III et al., "inhibition of DNA Binding Proteins by Oligonucleotide-Directed Triple Helix Formation", Science, 245, 725-730 (1989); *Science, 245,* 967-971 (1989) and *Science 249,* 73-75 (1990).

Griffin and Dervan, "Recognition of Thymine-Adenine Base Pairs by Guanine in a Pyrimidine Triple Helix Motif", Science, 245, 967-971 (1989).

Strobel and Dervan, "Site-Specific Cleavage of a Yeast Chromosome by Oligonucleotide-Directed Triple-Heliz Formation", Science 249, 73-75 (1990).

Symons, *Nucleic Acid Probes,* CRC Press, Inc., Boca Raton, Fla. (1989).

Gamper et al., "Reverse Southern Hybridization", *Nucleic Acids Research, 14,* 9943 (1986).

Knorre et al., "Complementary-Addressed (Sequence Specific) Modification of Nucleic Acids", Prog. *Nucleic Acids Res. Mol. Biol., 32,* 291 (1985).

(List continued on next page.)

*Primary Examiner*—Amelia Burgess Yarbrough
*Attorney, Agent, or Firm*—Hoffmann & Baron

[57] ABSTRACT

A sequence directed reagent is constructed by conjugating a methyl silyloxy aromatic derivative to a hexamethylamino linker attached to either the 5' or 3' terminus of an oligonucleotide. Annealing this modified fragment of DNA to its complementary sequence allows for target modification subsequent to ionic activation. The product of this reaction is a covalent crosslink between the reagent and target strands resulting from an alkylation of DNA by the activated silyloxy aromatic derivative. In a preferred embodiment, a nitrophenyl group is attached to the methyl group of the silyloxy aromatic derivative. This reagent is similarly linked to an oligonucleotide probe. Activation of this probe linked alkylating agent by an ionic signal, (X) which may naturally occur, or may be introduced into the media containing the target molecule, such as by the introduction of a salt (MX).

30 Claims, 4 Drawing Sheets

O NH Si O X $M^+X^-$ O NH O

OTHER PUBLICATIONS

Webb et al., "Sequence-Specific Crosslinking of Deoxyoligonucleotides via Hybridization-Triggered Alkylation", J. Am. Chem., Soc., 108, 2764-2765 (1986).
Meyer et al., "Efficient, Specific Crosslinking and Cleavage of DNA by Stable, Synthetic Complementary Oligonucleotides", J. Am. Chem. Soc., 111, 8517.
Van Houten et al., "Action Mechanism of ABC Excision Nuclease on a DNA Substrate Containing a Psoralen Crosslink at a Defined Position", Proc. Nat'l. Acad. Sci. (USA), 83, 8077 (1986).
Lee et al., "Interaction of Psoralen-Derivatized Oligodeoxyribonucleoside Methylphosphonates with Single-Stranded DNA", Biochemistry, 27 3197-3203 (1988).
Chatterjee and Rokita "Inducible Alkylation of DNA Using an Oligonucleotide Quinone Conjugate", J. Am. Chem. Soc., 112, 6397 (1990).
Ramage et al., "Solid Phase Peptide Synthesis: Fluoride Ion Release of Peptide from the Resin", Tet. Lett., 28, 4105-4108 (1987).
Mullen and Barany "A New Fluoridolyzable Anchoring Linkage for Orthogonal Solid Phase Peptide Synthesis", J. Org. Chem., 53, 5240 (1988).
Trahanovsky et al., "Observation of Reactive o-Quinodimethanes by Flow NMR", J. Am. Chem. Soc., 110, 6579 (1988).
Angle and Turnbull, "p-Quinone Methide Initiated Cyclization Reactions", J. Am. Chem. Soc., 111, 1136 (1989).
Wahl et al., "Northern and Southern Blots", *Methods Enz.*, 152, 572-573 (1987).
Higuchi et al., "DNA Typing from Single Hairs", *Nature,* 332, 543-546 (1988).
Conner et al., "Detection of Sickle Cell B$^s$-Globin Allele by Hybridization with Synthetic Oligonucleotides", Proc. Nat'l. Acad. Sci USA, 80, 278-282 (1983).
Gebeyehu et al., "Novel Biotinylated Nucleotide-Analogs for Labelling and Colormetric Detection of DNA", Nucl. Acids Res., 15, 4513-4534 (1987).
Jager et al., "Oligonucleotide N-Alkyl-phosphotamides: Synthesis and Binding to Polynucleotides", Biochemistry, 27, 7237-7246 (1988).
Cocuzza, "Total Synthesis of 7-Iodo-2', 3'-Dideoxy-7-Deazpurine Nucleosides, Key Intermediates in the Preparation of Reagents for the Automated Sequencing of DNA", Tet. Lett., 29, 4061-4064 (1988).
Hanna et al., "Synthesis and Characterization of 5-[(-4-Azidophenacyl) thio] uridine 5'-Triphosphate, a Cleavable Photo-Cross Linking Nucleotide Analogue", *Biochemistry, 28,* 5814-5820 (1989).
Gibson et al., "Synthesis and Application of Derivatizable Oligonucleotides" Nucl. Acids Res., 15, 6455-6467 (1987).
Nelson et al., "A New and Versatile Reagent for Incorporating Multiple Primary Aliphatic Amines Into Synthetic Oligonucleotides", Nucl. Acid Res., 17, 7179-7186, (1989).
Agrawal et al., "Oligodeoxynucleoside Phosphoramidates and Phosphorothioates as Inhibitors of Human Immunodeficiency Virus", Proc. Nat'l. Acad. Sci. USA., 85, 7079-7083 (1988).
Raval et al., *J. Univ. Bombay, 7, Pt. 3,* 184 (1938); CA 33, 3779 (1939).
Ramage et al., Tetrahedron Letters, 28, 4105-4108 (1987).
Dreyer et al., *Proc. Nat'l. Acad. Sci. USA, 82,* 968-972 (1985).
Chu et al., *Proc. Nat'l. Acad. Sci. USA, 82,* 963-967 (1985).
Mack et al., *J. Am. Chem. Soc., 110,* 7572-7574 (1988).

IONIC STRENGTH TRIGGERS SOLVOLYSIS TO FORM THE QUINONE METHIDE

| | | | | | | | | |
|---|---|---|---|---|---|---|---|---|
| 100mM cation | $K^+$ | $K^+$ | $K^+$ | $Li^+$ | $Na^+$ | $Cs^+$ | $(Bu)_4N^+$ | $K^+$ |
| 100mM anion | $Cl^-$ | $Br^-$ | $P_i$ | $F^-$ | $F^-$ | $F^-$ | $F^-$ | $ClO_4^-$ |

ION TRIGGERED ALKYLATION OF BIOLOGICAL TARGETS BY SILYLOXY AROMATIC AGENTS

BACKGROUND OF THE INVENTION

1. Field of the Invention

This invention relates to silyloxy aromatic alkylating agents that include a probe specific for biological targets. The alkylating agent is activated for reaction by an increase in ionic strength.

2. Background of the Related Art

Currently prescribed chemotherapeutic agents acting at the level of DNA are often effective, but their therapeutic index is quite poor, limited by the lack of target specificity. An international research effort has been underway using a wide range of techniques to develop a gene specific drug—a "magic bullet" that is aimed at single DNA sequence within a cell.

The technological advances allowing for facile DNA synthesis have produced innumerable protocols which rely on custom oligonucleotides, used as probes to screen for complementary sequences within plasmids, chromosomes and DNA libraries. See for example, Landegren et al., 37 DNA Diagnostics-Molecular Techniques and Automation", *Science*, 242, 229 (1988). The specificity of oligonucleotide hybridization has been utilized for "antisense" methods controlling selective expression of genes both in vivo and in vitro. For example, see Miller et al., "Oligonucleotide Inhibitors of Gene Expression in Living Cells: New Opportunities in Drug Design", *Ann. Reports in Med. Chem.*, 23, 295 (1988). Sequence recognition by the binding of probes most often depends on only the non-covalent forces of hydrogen bonding formed between complementary base pairs. Complexation of this type is quite sufficient for many applications, but covalent stabilization of duplex structures could simplify many of the current protocols and provide new opportunities for processing DNA in a sequence specific manner.

Messenger RNA has become a viable target for inhibiting the expression of a desired gene in vivo. See for example, Toulmé et al., "Antimessenger oligodeoxyribonucleotides: an alternative to antisense RNA for artificial regulation of gene expression - a review", *Gene*, 72, 51–58 (1988); and, Stein et al., "Oligodeoxyribonucleotides as Inhibitors of Gene Expression: A Review", *Cancer Research*, 48, 2659–2668 (1988). Compounds created for this selective reaction have drawn from the advances in site specific modification of DNA, for example see: Barton, "Metals and DNA: Molecular Left-Handed Complements", *Science*, 233, 727–734 (1986), and Dervan, "Design of Sequence-Sepcific DNA-binding molecules"*Science*, 232, 464–471 (1986). Use of such compounds also depends on the synthesis of metabolically stable oligonucleotides that can transverse cell membranes. For example, see: Blake et al., "Hybridization Arrest of Globin Synthesis in Rabbit Reticulocyte Lysates and Cells by Oligodeoxyribonucleoside Methylphosphonates", *Biochemistry*, 24, 6139–6145 (1985). Also, see Agrawal et al., "Oligodeoxynucleoside phosphoramidates and phosphorothioates as inhibitors of human immunodeficiency virus", *Proc. Nat'l. Acad. Sci. U.S.A.*, 85, 7079–7083 (1988).

Only recently introduced, the technique of oligonucleotide-directed irreversible DNA modification holds great potential as an in vitro tool for molecular biologists. See for example, Dervan, "Design of Sequence-Specific DNA-Binding Molecules", *Science*, 232, 464–471 (1986); and Iverson et al, in "Nonenzymatic Sequence-Specific Cleavage of Single-Stranded DNA to Nucleotide Resolution. DNA Methyl Thiolether Probes", *J. Am. Chem. Soc.*, 109, 1241–1243 (1987). Site specificity is enforced by the hybridization of the oligomer-reactant to its complement sequence prior to reagent action. Target selectivity can then be conferred, in theory, to most reactive compounds by attaching them to oligonucleotides. The required prehybridization step, however, generally limits this technique's applicability to accessible single strand polynucleotide targets or duplex probes when triple helical formation is possible, see Maher III et al., "Inhibition of DNA Binding Proteins by Oligonucleotide-Directed Triple Helix Formation", *Science*, 245, 725–730 (1989); *Science* 245, 967–971 (1989); and *Science*, 249, 73–75 (1990).

Site-directed covalent modification is also constrained by the nature of the reactive group incorporated into the oligomer. Although a large number of reactive appendages are available for related use in vitro, as reported by Iverson et al., *J. Am. Chem. Soc.*, 109 (1987) supra; and by Dervan, *Science*, 232 (1986) supra, only a limited set of these may apply in a controlled activated manner, either in vitro or for in vivo use.

Sequence recognition between synthetic oligonucleotides and macromolecular DNA represent the keystone of numerous techniques required in molecular biology; for example see: Symons *Nucleic Acid Probes*, CRC Press, Inc., Boca Raton, Fla. (1989). The fidelity of this process is typically determined only by the hydrogen bonds formed between complementary bases of double and triple helical DNA. Such associations are sufficient for most applications but covalent stabilization of a target-probe complex could simplify a variety of protocols including those used to diagnose genetic, malignant and infectious diseases; i.e. see discussions by Landegren et al., "DNA-Diagnostic, Molecular Techniques and Automation", *Science*, 242, 229 (1988); and Gamper et al., "Reverse Southern Hybridization" *Nucleic Acids Research*, 14, 9943 (1986).

A general method for this cross-linking has been demonstrated with the construction of oligonucleotide-directed alkylating agent, reported by Knorre et al., "complementary-Addressed (Sequence-Specific) Modification of Nucleic Acids", *Prog. Nucleic Acids Res. Mol. Biol.*, 32, 291 (1985); Webb and Matteucci, "Sequence-Specific Crosslinking of Deoxyoligonucleotides via Hybridization-Triggered Alkylation", *J. Am. Chem. Soc.*, 108, 2764 (1986); Dervan, "Design of Sequence-Specific DNA-binding Molecules", *Science*, 232, 464 (1986); nd Meyer et al., "Efficient, Specific Crosslinking and cleavage of DNA by Stable, Synthetic Complementary Oligonucleotides", *J. Am. Chem. Soc.*, 111, 8517 (1989). However, limitations are placed on these reagents because of their inherent reactivity. Only mildly reactive species would allow for target recognition to proceed covalent modification. An alternative approach has relied on moieties that remain inert until triggered by a chemical or photochemical signal. For example, see: Van Houten et al., "Action Mechanism of ABC Excision Nuclease on a DNA Substrate Containing a Psoralen Crosslink at a Defined Position", *Proc. Natl. Acad. Sci.* (*U.S.A.*). 83, 8077 (1986); Lee et al., "Interaction of Psoralen-Derivatized Oligodeoxyribonucleoside Methylphosphonates with Single-Stranded DNA", *Biochemistry*, 27, 3197 (1988); Iverson et al., "Nonenzymatic Sequence-Specific Cleavage of Single-Stranded DNA to Nucleotide Resolution. DNA Methyl Thiolether Probes", *J. Am. Chem. Soc.*, 109, 1241 (1987); Chatterjee and Rokita "Inducible Alkylation of DNA Using an Oligonucleotide-Quinone Conjugate" *J. Am. Chem. Soc.* 112, 6397 (1990); and also see co-pending patent application U.S. Ser. No. 07/442,947, filed on Nov. 29, 1989, now patented, the disclosure of which is incorporated by reference herein.

Organosilane compounds have been used as intermediates in the formation of quinone methides in aprotic solvents. For example, see Ramage et al., "Solid Phase Peptide synthesis: Fluoride Ion Release of Peptide from the Resin", *Tet. Lett.*, 28, 4105 (1987); Mullen and Barany "A New Fluoridolyzable Anchoring Linkage for Orthogonal Solid Phase Peptide Synthesis", *J. Org. Chem.*, 53, 5240 (1988); Trahanovsky et al., "Observation of Reactive o-Quinodimethanes by Flow NMR", *J. Am. Chem. Soc.*, 110, 6579 (1988); and Angle and Turnbull, "p-Quinone Methide Initiated Cyclization Reactions", *J. Am. Chem. Soc.*, 111, 1136 (1989).

Yabusaki et al., in PCT Published Application No. WO 85/02628 describe cross-linking agents for binding an oligonucleotide probe to a target DNA or RNA molecule. Three types of cross-linking agents are described, including "bi-functional photoreagents", "mixed chemical and biochemical bifunctional reagents" and "bifunctional chemical cross-linking molecules". The bifunctional photoreagents contain two photochemically reactive sites that bind covalently to the probe and to the target molecules. The mixed chemical and photochemical bifunctional reagent is bound non-photochemically to the probe molecule, followed by photochemical binding to the target molecule. Non-photochemical binding is described as a chemical reaction such as alkylation, condensation or additional. Bifunctional chemical cross-linking molecules are said to be activated either catalytically or by high temperature following hybridization.

Although Yabusaki et al. generally hypothesize the concept of a bifunctional photochemical reagent and a mixed chemical and photochemical reagent, there is no specific description of these molecules. All of the reagents they describe are well known photochemical reagents, these include the psoralen derivatives, including furocoumarins, the benzodipyrone derivatives, and the bis-azide derivatives. None of these molecules, however, work on the basis of ionic activation. These reagents, especially the psoralen derivatives are toxic, causing severe burning of the organism after exposure to sunlight. Finally, the covalent crosslinks formed by psoralens are not permanent, rather, they are degraded by UV irradiation.

Two recent articles reported the use or psoralen crosslinks of DNA substrates, the first by Van Houten et al., in "Action mechanism of ABC excision nuclease on a DNA substrate containing a psoralen crosslink at a defined position", *Proc. Nat'l. Acad. Sci. U.S.A.*, 83, 8077–8081 (1986), and the second by Lee et al., in "Interaction of Psoralen-Derivatized Oligodeoxyribonucleoside Methylphosphonates with Single-Stranded DNA", *Biochemistry*, 27, 3197–3203 (1988). Both articles reported covalent cross-linking between the DNA molecule and a complementary oligomer that contains a psoralen derivative. The covalent binding of the psoralen derivative to the DNA molecule was activated by UV irradiation. Accordingly, just like the Yakusaki patent application, the covalent crosslinks, formed by psoraless are not permanent, being degraded by UV irradiation.

The techniques of Northern and Southern blotting are two of the most powerful and frequently used procedures in molecular biology, see Wall et al., "Northern and Southern Blots", *Methods Enz.*. 152, 572–573 (1987). Yet the necessary manipulations are time consuming and are not likely to be automated under current technology. Often the polynucleotide (RNA, DNA) under analysis must first be fractionate by size, transferred onto a solid support and then treated through a series of steps to ensure only specific binding of a probe. Detection of the hybridized products usually depends on radiolabelling, heavy metal derivatization or antibody complexation. The methods of blotting have been a staple of basic research, and now also serve in an ever increasing number of commercial kits used to diagnose genetic malignant and infectious diseases (see Landegren et al. *Science*, 242, (1988) supra). Related advances have also allowed these processes to aid in forensic science, see Higuchi et al., "DNA Typing from Single Hairs", *Nature*, 332, 543–546 (1988); and, the Human Genome Project, see Conner et al., "Detection of Sickle Cell $\beta^s$-Globin Allele by Hybridization with Synthetic Oligonucleotides", *Proc. Nat'l. Acad. Sci. U.S.A.*, 80, 278–282 (1983).

Psoralens have been used to randomly crosslink duplex DNA during hybridization in order to facilitate Southern Blotting procedures. This new test is referred to as Reverse Southern blotting. For example, see Gamper et al., in "Reverse Southern Hybridization", *Nucl. Acids Res.*, 14, 9943 (1986). Other biochemical and reduction activated reagents are needed to replace or complement psoralens for sequence detection and to provide an alternate set of conditions for duplex stabilization.

Accordingly, none of the related art describes or suggests using ionic activation with an aromatic silyloxy alkylating agents in order to permanently alkylate a biological molecule such as DNA.

Therefore, it is an object of the present invention to provide a new class of ionically activated alkylating probes which form a permanent covalent crosslink.

Another object of the present invention is to provide an ionically activated alkylating probe which can be used in vivo.

A further object of the present invention is to provide a new class of ionically activated Reverse Southern blotting reagents for conjugating and permanently crosslinking target oligonucleotides and facilitate blotting procedures, sequence detection and nucleic acid fragmentation.

SUMMARY OF THE INVENTION

These and other objects are achieved by the present invention which provides a process and probe for selectively and permanently alkylating a target molecule. The process includes the steps of providing a probe, such as an oligonucleotide, for recognizing a predetermined binding site on a target molecule, such as a DNA sequence which is complementary to the probe. Providing a silyloxy aromatic derivative for linking to the probe. Linking the probe to the silyloxy aromatic derivative to form a targeted alkylating agent. The targeted alkylating agent has the general formula:

(1)

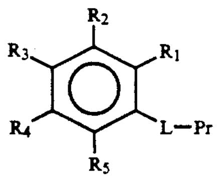

When $R_1$ = —$OSi(R_6R_7R_8)$, then $R_2$ and/or $R_4$ can be = —$CHR_9X$.

When $R_2$ = —$OSi(R_6R_7R_8)$, then $R_1$, $R_3$ and/or $R_5$ can be = —$CHR_9X$.

When $R_3$ = —$OSi(R_6R_7R_8)$, then $R_2$ and/or $R_4$ can be = —$CHR_9X$.

When $R_4$ = —$OSi(R_6R_7R_8)$, then by symmetry $R_4$ is equivalent to $R_2$ as described above.

When $R_5$ = —$OSi(R_6R_7R_8)$, then by symmetry $R_5$ equivalent to $R_1$ as described above.

$R_6$, $R_7$, $R_8$ = various alkyl or aromatic groups; and

X = leaving group. wherein $R_p$ can be H, or an organic derivative, such as an aliphatic group or an alkyl group In which $CHR_9X$ is positioned on any of the carbon atoms of the ring structure; L is a linking group for attachment to a probe which may be positioned at any carbon atom of the ring, and Pr is a probe for binding to a target molecule. Preferably, the targeted alkylating agent of the present invention has the general formula.

(2)

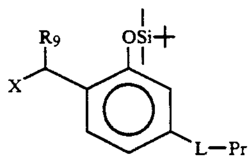

The alkylating agent need not be restricted to a single aromatic ring, for example it may have a multi-ring structure, (3)

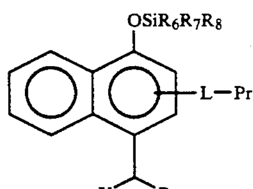

or, (4)

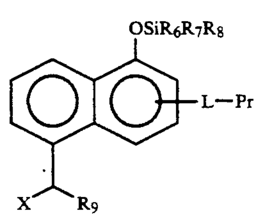

The targeted alkylating agent is then introduced into a system containing the target molecule to allow the probe to associate, i.e. hybridize, with a target molecule and localize the linked silyloxy aromatic derivative near the target molecule. The targeted alkylating agent is activated by an ionic signal which causes covalent bonding between the aromatic derivative proximal to the association site of the probe with a target molecule.

In a preferred embodiment, the X group is a displaceable reactive moiety attached to an alkyl group positioned on a carbon atom of the silyloxy aromatic ring. Examples of such groups include Br, Cl, F, I, OAc, OH, $OSO_2CH_3$, $OSO_2C_6H_4CH_3$-p, $OCH_2CH_3$, $OCONHCH_3$, $OCONHCH_2CH_2R$, —$OC_6H_4HO_2$(nitro-phenol) $C_6H_5O$ (phenol), and $C_6H_5S$ (thio-phenol). The alkylating agent is activated by a reductive signal which either naturally occurs, or by a signal that is introduced into the media containing the target molecule.

For a better understanding of the present invention reference is made to the foregoing description made in conjunction with the figures, the scope of which is defined in the claims.

DETAILED DESCRIPTION OF THE INVENTION

Figure 1:
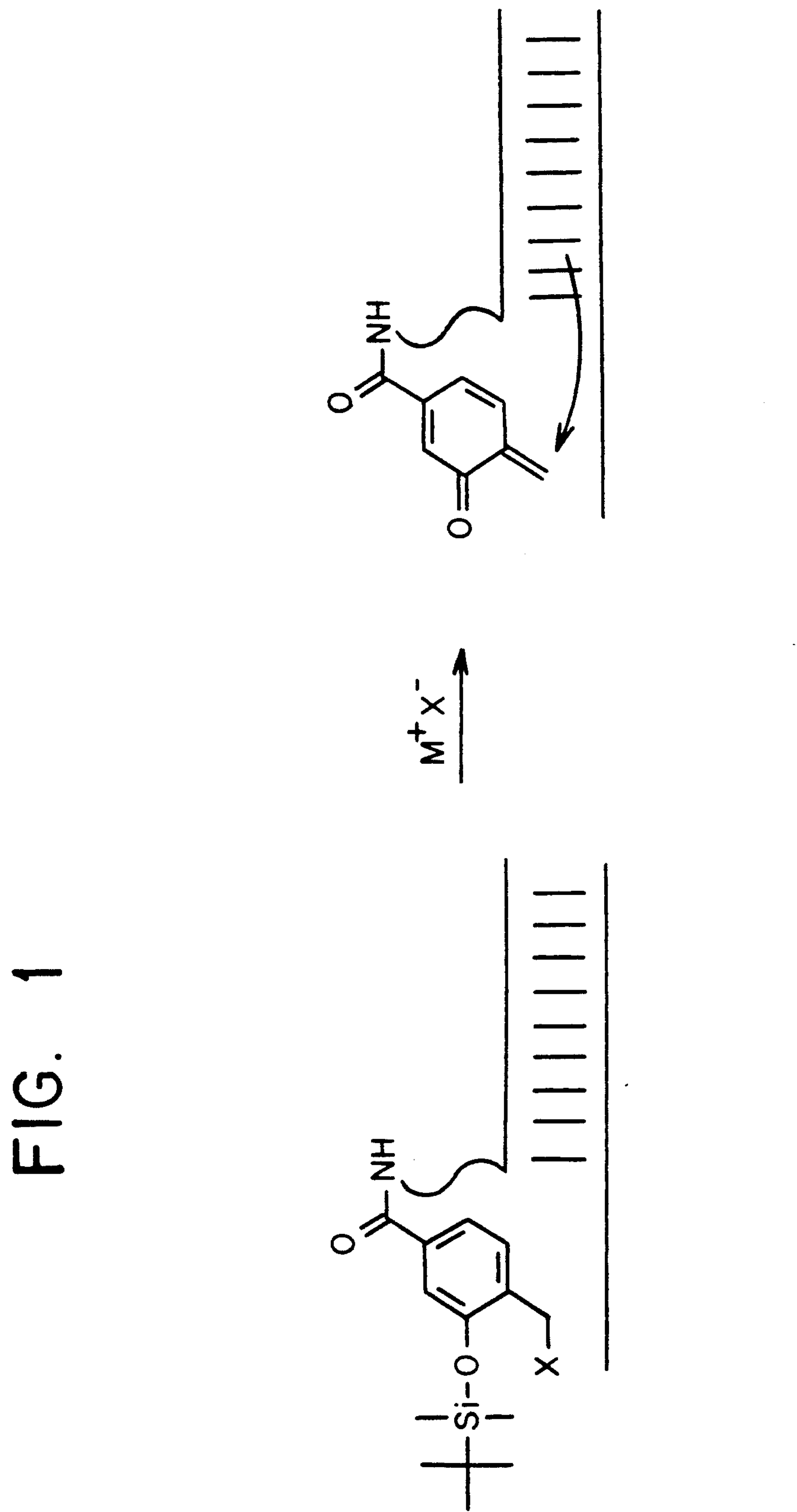
FIG. 1 illustrates ionic activation ($M^+X^-$) of a conjugated target (T) and probe (Pr) linked to a preferred silyloxy aromatic molecule to create the reactive intermediate of the present invention generated for alkylation of the target DNA.

In accordance with a preferred embodiment of the present invention an aromatic derivative is conjugated to a probe which has potential for selective alkylation of target biological molecules. It is believed that the conjugated aromatic derivatives will not react indiscriminately with biological materials other than the target molecules.

The novel aromatic alkylating probe composition has the following generalized formula:

(1)

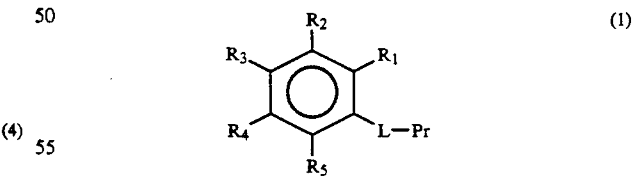

When $R_1$ = —$OSi(R_6R_7R_8)$, then $R_2$ and/or $R_4$ can be = —$CHR_9X$.

When $R_2$ = —$OSi(R_6R_7R_8)$, then $R_1$, $R_3$ and/or $R_5$ can be = —$CHR_9X$.

When $R_3$ = —$OSi(R_6R_7R_8)$, then $R_2$ and/or $R_4$ can be = —$CHR_9X$.

When $R_4$ = —$OSi(R_6R_7R_8)$, then by symmetry $R_4$ is equivalent to $R_2$ as described above.

When $R_5$ = —$OSi(R_6R_7R_8)$, then by symmetry $R_5$ equivalent to $R_1$ as described above.

$R_6$, $R_7$, $R_8$=various alkyl or aromatic groups; and X=leaving group.

Wherein $R_p$ can be H, or an organic derivative, such as an aliphatic group or an alkyl group.

In which $CHR_9X$ is positioned on any of the carbon atoms of the ring structure; L is a linking group for attachment to a probe which may be positioned at any carbon atom of the ring, and Pr is a probe for binding to a target molecule. Preferably, the targeted alkylating agent of the present invention has the general formula.

(2)

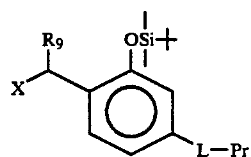

The alkylating agent need not be restricted to a single aromatic ring, for example it may have a multi-ring structure, (3)

(4)

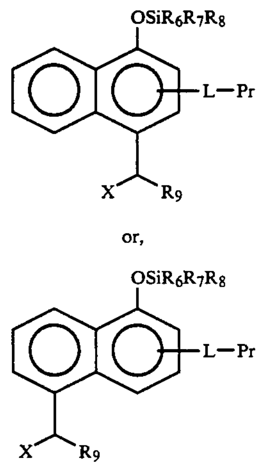

The targeted alkylating agent is then introduced into a system containing the target molecule to allow the probe to associate, i.e. hybridize, with a target molecule and localize the linked silyloxy aromatic derivative near the target molecule. The targeted alkylating agent is activated by an ionic signal which causes covalent bonding between the aromatic derivative proximal to the association site of the probe with a target molecule.

In these embodiments, the silyloxy aromatic probe alkylates a target molecule after activation by an ionic signal. In these embodiments X is a leaving group connected to an alkyl chain positioned on an aromatic ring structure. The alkyl chain is connected at one end to the aromatic ring and includes $R_9$, an organic derivative.

Thus X may include one of the leaving groups, such as Cl, Br, F, I, OCOR, OH, $OSO_2CH_3$, $OSO_2C_6H_4CH_3$-p, OR, OCONHR, $OCONHCH_2CH_2R$, $C_6H_4NO_3$ (nitro-phenol), $C_6H_5O$ (phenol), and $C_6H_2S$ (thio-phenol).

In all of these compositions, the linking group L is made up of a chain $R_{10}$—$R_{11}$—$R_{12}$—. Generally the $R_{10}$ group may include a group for linking to the silyloxy aromatic derivative including NH, S, O or $CH_2$. The $R_{11}$ group can include any spacer group which can link $R_{10}$ and $R_{12}$, such as an alkyl chain. The $R_{12}$ group is any group which can link to a modified oligonucleotide or other probe examples of these are $NH_2$, SH, OH and COOH. The probe Pr includes any localizing moiety, such as an oligonucleotide, protein, antibody, sugar or other molecule that preferentially localizes to an organic molecule, including DNA, RNA, or protein. The oligonucleotide, whether DNA or RNA may be linked to $R_{12}$ at either its 5′ or 3′ terminus.

Alternatively, the oligonucleotide may be linked to $R_{12}$ at any oligonucleotide base, or phosphoribose backbone suitably modified in accordance to the methods described by the following publications, the disclosure of which is incorporated by reference herein:

1. Gebeyehu et al., "Novel Biotinylated Nucleotide-Analogs for Labelling and Colorimetric Detection of DNA", *Nucl. Acids Res.*, 15, 4513–4534 (1987).

2. Jàger et al., "Oligonucleotide N-Alkylphosphotamides: Synthesis and Binding to Polynucleotides", *Biochemistry*, 27, 7237–7246 (1988).

3. Cocuzza, "Total Synthesis of 7-Iodo-2′,3′-Dideoxy-7-Deazpurine Nucleosides, Key intermediates in the Preparation of Reagents for the Automated Sequencing of DNA", *Tet. Lett.*, 29, 4061–4064 (1988).

4. Hanna et al., "Synthesis and Characterization of 5-[(4-Azidophenacyl)thio]uridine 5′-Triphosphate, a Cleavable Photo-Cross-Linking Nucleotide Analogue", *Biochemistry*, 28, 5814–5820 (1989).

5. Gibson et al., "Synthesis and application of derivatizable oligonucleotides", *Nucl. Acids Res.*, 15, 6455–6467 (1987).

6. Nelson et al., "A New and Versitile Reagent for Incorporating Multiple Primary Aliphatic Amines Into Synthetic Oligonucleotides.", *Nucl. Acid Res*, 17, 7179–7186, (1989).

In a preferred embodiment of the invention, described in Examples 1 and 2, the silyloxy aromatic alkylating probe is activated by an ionic signal. For in vitro use the preferred ionic signals are KF, NaF, CsF and other salts (MX), defined as salts of a metal (M) and an anion (X). These, however, are not the only possible ionic triggering agents. Rather, the triggering signal is dependent on a general increase in ionic strength. Accordingly, silyl containing reactive centers, such as $Si{:}R_6R_7R_8$, as defined above, can be used for both in vitro and in vivo uses.

The preferred embodiment of the present invention has the following structure:

(5)

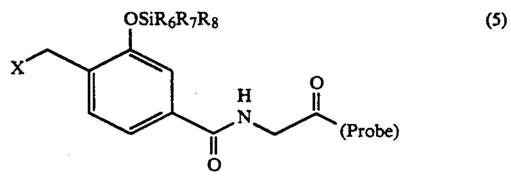

Another embodiment (6) which was attempted includes:

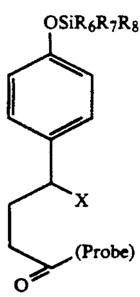

(6)

This embodiment, however, proved too reactive.

Another embodiment (7) was attempted, but it did not couple well to the probe.

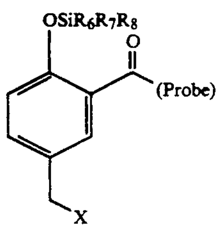

(7)

Another embodiment (8) was too unreactive, it would only work in non-aqueous systems.

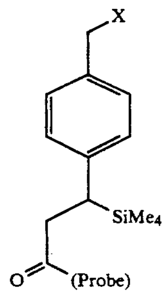

(8)

The present invention also describes a process for selectively alkylating a target molecule. A great number of useful clinical and laboratory applications for which this process may be applied are described for somewhat related processes in PCT published Application No. WO 85/02628 to Yabusaki et al., the disclosure of which is incorporated by reference herein. Also the process of Reverse Southern Blotting is described generally in the Background of the Related Art, supra.

Generally, the process of this invention is carried out by first providing a probe for recognizing a predetermined binding site on a target molecule. The probe may include a strand of DNA, RNA, or a protein; or it may include any other molecule which can localize the probe to a target molecule. The process is carried out by providing a silyloxy aromatic derivative which is modified for linking to the probe molecule. The probe is then linked to the silyloxy aromatic derivative to create a targeted alkylating agent. The target alkylating agent is introduced into a system containing a target molecule and the probe associates with the target molecule localizing the linked silyloxy aromatic derivative near the target molecule. As illustrated in FIG. 1, crosslinking or covalent bonding is then initiated by activating the targeted alkylating agent by an ionic signal, such as KF, other salts MX, or the ionic signal can be the naturally occurring high ionic strength region localized around polyanionic nucleic acids. A covalent bond is then formed between the aromatic derivative and the target, proximal to the association site of the probe with the target molecule.

In one preferred embodiment, the linking step includes a step of adapting the silyloxy aromatic derivative by the addition of an acidic linking group which is capable of being modified for linking to the probe molecule. Preferably, an addition reaction of 3-mercaptopropionic acid, which includes activation of the acid by esterification with N-hydroxysuccinimide adapts the molecule for coupling to the probe. Preferably, the silyloxy aromatic derivative includes an arm $CHR_9X$, attached to the aromatic ring.

If in vivo use is desired, then suitably modified probes capable of transversing cell membranes are prepared, for example as described by Blake et al., "Hybridization Arrest of Globin Synthesis in Rabbit Reticulocyte Lysates and Cells by Oligodeoxyribonucleoside Methylphosphonates", *Biochemistry*, 24, 6139-6145 (1985); and, by Agrawal et al., "Oligodeoxynucleoside phosphoramidates and phosphorothioates as inhibitors of human immunodeficiency virus", *Proc. Nat'l. Acad. Sci. U.S.A.*, 85 7079-7083 (1988). These probes are then attached to the activated esters.

The following Examples further illustrate the various features of the invention, and are not intended in any way to limit the scope of the invention which is defined in the appended claims.

In these Examples, we have shown that a preferred probe, as described above causes selective alkylation of a DNA target, which has been ionically activated after the probe has hybridized with the target DNA sequence.

EXAMPLE 1

Preparation of Silyloxy Aromatic Ionically Inducible Alkylating Linked Probe An ionic induced silyloxy aromatic alkylating linked probe was prepared in accordance with the invention. The probe was tested in vitro using a synthetic DNA target strand. The steps followed in the synthesis of a representative silyloxy aromatic ion-induced alkylating probe for coupling to the 5' terminus of an oligonucleotide are generally shown in Scheme A.

SCHEME A

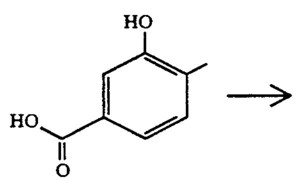

-continued

SCHEME A

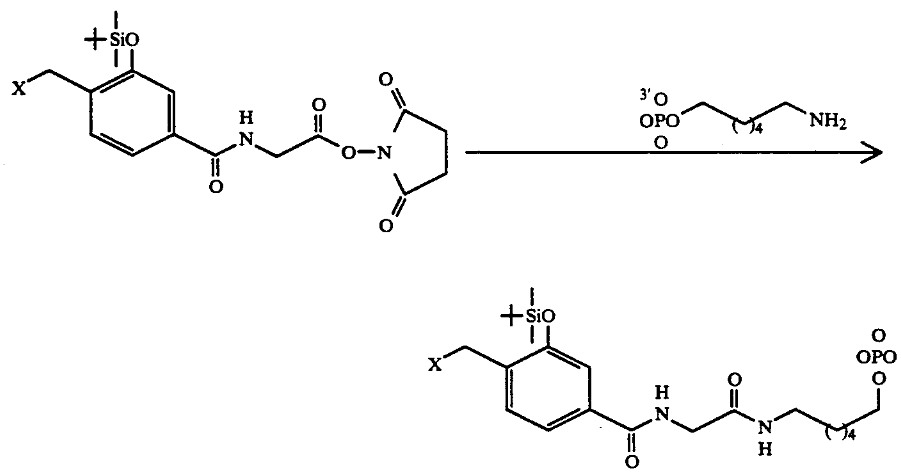

A parallel series of steps followed in the synthesis of a representative silyloxy aromatic ion induced alkylating probe for coupling to the 3' terminus of an oligonucleotide are shown in Scheme B.

SCHEME B

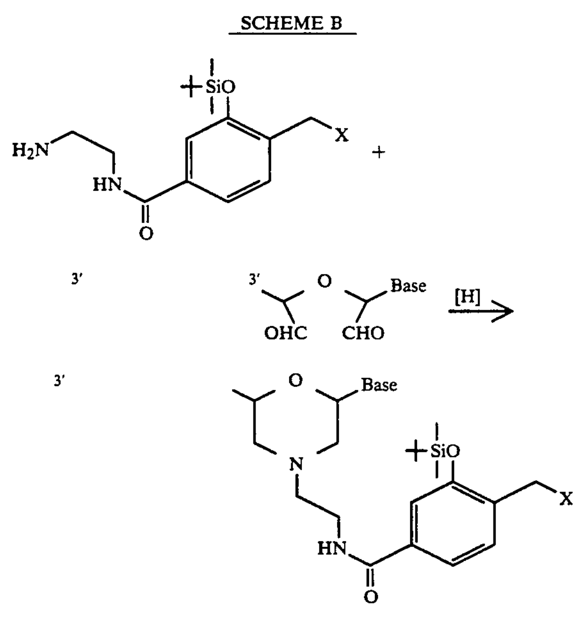

EXAMPLE 2

Preparation of the preferred silyloxy aromatic system suitable for coupling to a probe-linker species (L-Pr)

The following general Scheme (1) illustrates the steps taken in the synthesis of the preferred silyloxy aromatic molecules which are suitable for coupling to probe (Pr) linker (L) species, and directing the ionically inducible covalent crosslinking system to a desired target (T). The method described in Scheme 1 is general enough for the preparation of a number of useful derivatives of 1.7.

SCHEME 1

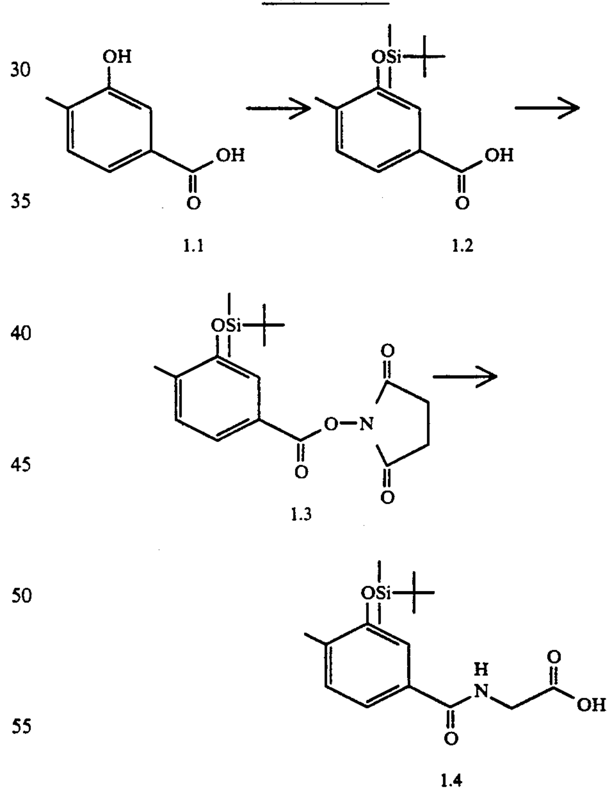

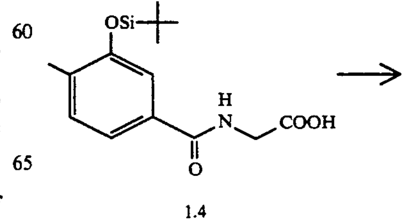

-continued
SCHEME 1

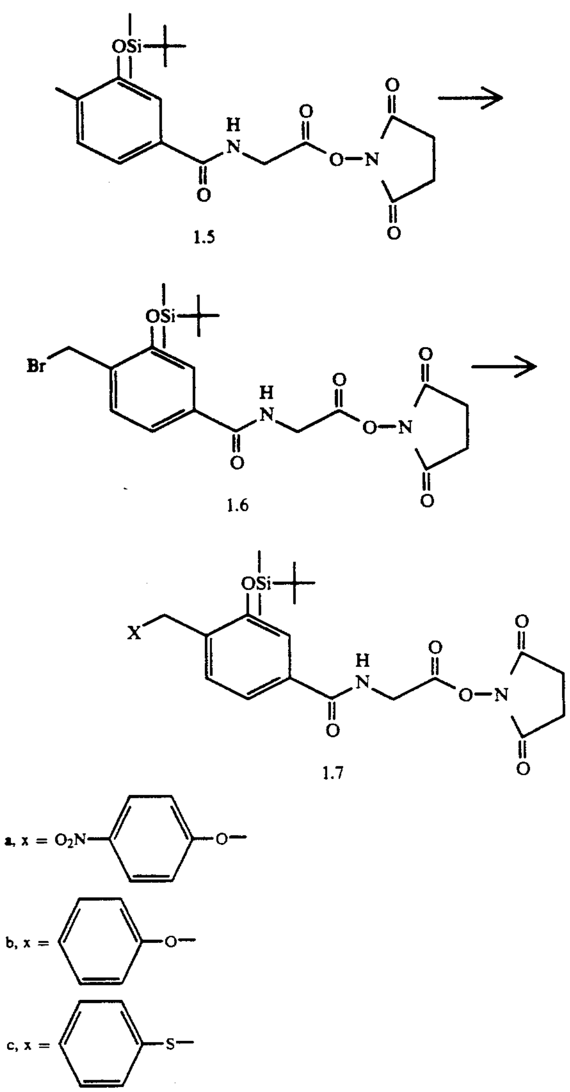

Protocol 1.1: Synthesis of the Silyl Protected 1,2,5-Trisubstituted Phenol:

Materials and Methods for the synthetic procedures. Proton magnetic resonance ($^1$H NMR) spectra were recorded on a QE-300 spectrometer. Chloroform-d was used as a solvent and TMS as reference. UV/Vis spectra were measured with a Perkin-Elmer Lambda 5 spectrophotometer and mass spectra were obtained with a HP 598A mass spectrometer. Flash chromatography is a commonly used purification technique described by Still et al. *J. Org. Chem.* 43, 2923–2925 (1978) and 230–400 mesh silica gel was used. Thin-layer chromatography (TLC) analysis utilized Machery-Nagel polygram Sil G/UV silica gel plates. Tetrahydrofuran (THF) was distilled from sodium, and acetonitrile was distrilled from $CaH_2$ immediately prior to use. Dimethyl formamide (DMF), $CCl_4$ and triethylamine were stored over Linde 4-A molecular sieves at least two days prior to use. Other materials identified in these Examples were obtained from commercial suppliers and used without further purification., 3-t Butyldimethylsiloxyl-4-methylbenzoic acid (Compound 1.2). As shown in Scheme I t-Butyldimethylsilyl chloride (3.32 g, 22.1 mmol) was added to a solution of Compound 1.1, shown in Scheme I (1.12 g, 7.4 nmol) and triethylamine (1.79 g, 16.2 mmol) in THF. The mixture was heated at 40° C. overnight. After the reaction mixture was allowed to cool to room temperature, the triethylammonium chloride was filtered out. The filtrate was then diluted with ether (50 mL) and a few drops of distilled water was added and stirred at room temperature for five hours. After evaporation of the solvent, the product was purified by flash silica chromatography (ethyl acetate:hexanes, 1:3) to yield 1.60 g (81.5%) of -a white solid: $^1$H NMR δ 7.49 (s, 1H), 7.39 (s, 1H), 7.11 (d, 1H), 2,20 (s, 3H), 0.96 (s, 9H), 0.31 (s, 6H).

3 t-Butyldimethylsiloxyl-4-methylbenzoic acid N-hydroxysuccinimide ester (Compound 1.3) Dicyclohexylcarbodiimide (DCC, 1.17 g, 5.7 mmol) was added to a solution of N-hydroxysuccinimide (0.28g, 7.1 mmol) and 1.2 (1.27 g, 4.8 mmol) in DMF (50 mL) and stirred overnight at 4 C. This mixture was then diluted with ether (50 mL) and water (50 mL), filtered and concentrated. The remaining residue was purified by flash silica chromatrography (ethyl acetate:hexanes, 1:3) to yield 1.13 g (65.3%) of a white solid: $^1$H NMR δ 7.60 (d, 1H), 7.41 (s, 1H), 7.18 (d, 1H), 2.83 (s, 4H), 2.23 (s, 3H), 0.96 (s, 9H), 0.18 (s, 6H). LRMS m/z 363 (M+), 217, 189, 85.

N-(3-t-Butyldimethylsiloxyl-4-methylbenzoyl) glycine (Compound 1.4). An aqueous solution (50 mL) of glycine (0.11 g, 1.5 mmol) was combined at room temperature with a solution of 1.3 (0.44 g, 1.2 mmol) in acetonitrile (50 mL) and triethylamine (0.14 g, 1.2 mmol). This mixture was manually shaken for two minutes and then washed with ether (50 mL). The aqueous phase was acidified to pH 2 with 6N HCl and extracted with ether (3×50 mL). The combined organic phases were evaporated and the product was purified by flash silica chromatography (ethyl acetate:hexanes, 1:1) to yield 0.31 g (74.6%) of a white solid: $^1$H NMR δ 7.26 (m, 3H), 6.64 (m, 1H), 4.02 (d, 2H), 2.20 (s, 3H), 0.98 (s, 9H), 0.22 (s,6H). LRMS m/z 323 (M+), 221, 149, 99.

N'-(3-t-Butyldimethylsiloxyl-4-methylbenzoyl)glycine-N-hydroxysuccinimide ester (Compound 1.5). The method described for the synthesis of Compound 1.3 was also used to produce Compound 1.5 (62.2% yield). $^1$HNMR δ 7.24 (m, 3H), 6.50 (m, 1H), 4.59 (d, 2H), 2.86 (s, 4H), 2.24 (s, 3H), 1.01 (s, 9H), 0.24 (s,6H). LRMS m/Z 420 (M+), 348, 190.

N'-(3-t-Butyldimethylsiloxyl-4-(bromomethyl)benzoyl) glycine N-hydroxysuccinimide ester (Compound 1.6). N-bromosuccinimide (NBS) (0.07 g, 0.4 mmol) was added to a solution of Compound 1.5 (0.12 g, 0.29 mmol)in $CCl_4$ (10 mL). The mixture was then maintained at 20° C. and irradiated with a 275 W sunlamp (Sears, #34-7105) for fifteen minutes. After the solid succinimide was filtered away, the filtrate was evaporated. The remaining residue was purified by flash silica chromatography (ethyl acetate:hexanes, 1:3) to yield 0.08 g (58.9%) of a white solid. $^1$HNMR δ 7.26 (m, 3H), 6.76 (m, 1H), 4.60 (d, 2H), 4.50 (s, 2H), 2.86 (s, 4H), 1.01 (s, 9H), 0.31 (s, 6H). LRMS m/z 344, 342, 263, 245.

N'-3-t-Butyldimethylsiloxyl-4-(p-nitrophenoxy)benzoyl glycine N-hydroxysuccinimide ester (Compound 1.7a). Potassium p-nitrophenolate (0.02 g, 0.2 mmol) was added to a solution of Compound 1.4 (0.08 g, 0.2 mmol) in freshly distilled acetonitrile (2 mL). The mixture was stirred at room temperature for one hour and then water and ether (10 mL of each) were added. The aqueous phase was washed with 3×10 mL of ether. The combined ether fractions were dried and the remaining residue was purified by flash silica chromatography to yield a yellowish solid (0.05 g, 59.4%). $^1$HNMR δ 8.32 (d, 2H), 7.60 (d, 2H), 7.37 (m, 3H), 6.52 (m, 1H), 5.53 (d, 2H), 5.18 (s, 2H), 2.67 (s, 2H), 1.02 (s, 9H), 0.30 (s, 6H). LRMS m/z 419, 349, 275, 189.

N'[3-t-Butyldimethylsiloxyl-4-(phenoxymethyl)benzoyl] glycine N-hydroxysuccinimide ester (Compound 1.7b). Potassium phenolate (0.01 g, 0.1 mmol) was added to a solution of Compound 1.6 (0.02 g, 0.1 mmol) in freshly distilled acetonitrile 2 mL). The mixture was stirred at room temperature for one hour and water and ether (10 mL of each) were added. The aqueous phase was washed 3×10 mL of ether. The combined ether fractions were dried and the remaining residue was purified by flash silica chromatography to yield a white solid (0.01 g, 49%), $^1$H NMR δ 7.56 (d, 2H), 7.32 (m, 6H), 6.72 (m, 1H), 5.17 (s, 2H), 4.60 (d, 2H), 2.66 (s, 4H), 1.01 (s, 9H), 0.29 (s, 6H).

N'-[3-t-Butyldimethylsiloxyl-4-thiophenoxymethyl)-benzoyl] glycine N-hydroxysuccinimide ester (Compound 1.7c). This was synthesized under equivalent procedure as described for Compounds 1.7a and 1.7b, above, the adaptation of which is well within the of those skilled in the art. $^1$H NMR δ 7.37 (m, 8H), 6.60 (m, 1H), 4.52 (d, 2H), 4.04 (s, 2H), 2.82 (s, 4H), 0.95 (s, 9H), 0.23 (s, 6H).

Protocol 1.2: Coupling the reactive centers (Compound 1.7) to a sequence directing oligonucleotide linker (L-Pr).

Materials and methods for coupling procedures. Oligonucleotides were synthesized by standard solid phase phosphoramidite methods on a Dupont Coder 300 (Department of Pharmacology SUNY at Stony Brook) and on a Biosearch instrument by Clontach Laboratories, Inc. (Palo Alto, Calif.). When necessary, the oligonucleotides were also purified and deprotected by standard procedures. Reverse phase (C-18) separation and analysis utilized a Varian 5000 HPLC controller, Varian 2050 variable wavelength detector, Hewlett Packard 3390A recording integrator and Spherex 5 μM C-18 column (Phenomenex). UV/VIS spectra were recorded on a Perkin Elmer Lamada-5 spectrophotometer.

Preparation of the oligonucleotide (Pr) derivatized at the 5' end with a hexamethylamino group (L-Pr). The hexamethylamino linker was attached to the 5' end of the nascent oligonucleotide (Pr, ACGTCAGGTGGCACT SEQ ID NO:1) during the last step of the solid phase synthesis by using a monomethyoxytrityl protected precursor supplied by Clontech Laboratories, Inc. The protecting group was released after the complete synthesis by treating the crude material with 80% acetic acid for 30 minutes. The free trityl derivative was removed by ether extraction and the oligonucleotide aminolinker derivative was stored as an aqueous solution (−20° C.) before coupling to the reactive centers.

Coupling the activated ester 1.7a to the aminolinker oligonucleotide probe (L-P). A solution of 2 mg Compound 1.7a in DMF (200 μL) was combined with a solution of L-Pr ($A_{260}$=3.0 absorbance units [AU]) in 0.25M 3-(N-morpholino)propanesulfonic acid at pH 7.5) (200 μL). This mixture was left undisturbed at 4° C. for 5 hours. The coupled product, designated Compound 1.7 a-L-Pr, was purified by reverse phase (C-18) chromatography using a gradient of 10% acetonitrile in 45 mM triethylammonium acetate pH 6 to 30% acetonitrile in 30 mM triethylammonium acetate pH 6 over 30 min (1 mL/min). The desired material eluted with a retention time of 23 min and, after collection, was immediately frozen and dried under high vacuum (20% yield based on recovered AU260)

Protocol 1.3: Preparation of target (T) and Modification of T with the reagent Compound 1.7a-L-Pr.

The target strand (T, AGTGCCACCTGACGTCTAAG SEQ ID NO:1) was prepared in the same manner as the oligonucleotide Pr described in Protocol 1.2. For product detection, T was labeled with $^{32}$P (*pT) in accordance with the procedures described by Maniatis et al., in *Molecular Cloning, A Laboratory Manual,* Cold Spring Harbor Laboratory, Cold Spring Harbor, N.Y. (1982).

Probe-target crosslinking and detection. The reaction between the probe (Compound 1.7a-L-Pr) and target sequences (T) was characterized in a standard reaction mixture (10 μL) containing 1 mM potassium phosphate pH 7, 6 nM 1.7a-L-P and 6 nM *pT (20 nCi). Samples were incubated at 4° C. for no less than lo min and then an aqueous solution of KF was added to a final concentration of 10–250 mM. This treatment activated the system for covalent crosslinking of the hybridized strands. This process was quenched after 10 min (4° C.) by addition of excess DNA (for example, T) and placing samples on dry ice. The volume of each sample was then reduced by 50% under high vacuum and 5 μL of 80% formamide was added in preparation for electrophoretic analysis.

Figure 2:
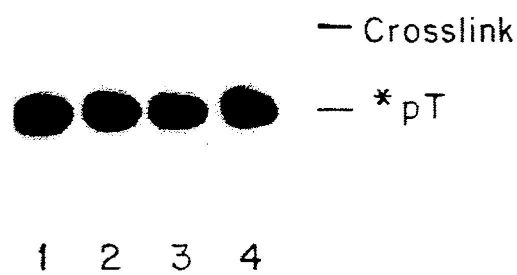
FIG. 2 is an autoradiogram of a denaturing polyacrylamide gel electrophoresis showing the ionic activated cross-linking reaction between a probe and a DNA target in accordance with the present invention, as discussed in Example 2, Protocol 1.3.

FIG. 2 shows an autoradiogram of a denaturing polyacrylamide gel (20%) that was used to demonstrate the successful application of Compound 1.7a-L-Pr. The material detected in lane 1 illustrates the migration of the unmodified target (*pT). The material in this lane was treated in the manner described above but the formamide was added to the incubation mixture before the DNA. This prevented hybridization and as a result, crosslinking was also prohibited. Destruction of the reactive appendage (Compound 1.7a of Compound 1.7a-L-Pr) by heat or premature activation (KF) also prevented the later reaction between probe and target. No crosslinked product was evident in lane 2 for which Compound 1.7a-L-Pr was heated to 60° C. (5 min) before incubation with *pT. Pretreatment of 1.7a-L-Pr with T (unlabelled) was also sufficient to prevent any secondary modification of DNA such as *pT (lane 3). Selective linking between *pT and Compound 1.7a-L-Pr was detected after KF was added to the hybridized complex of probe and target (lane 4).

Figure 3:
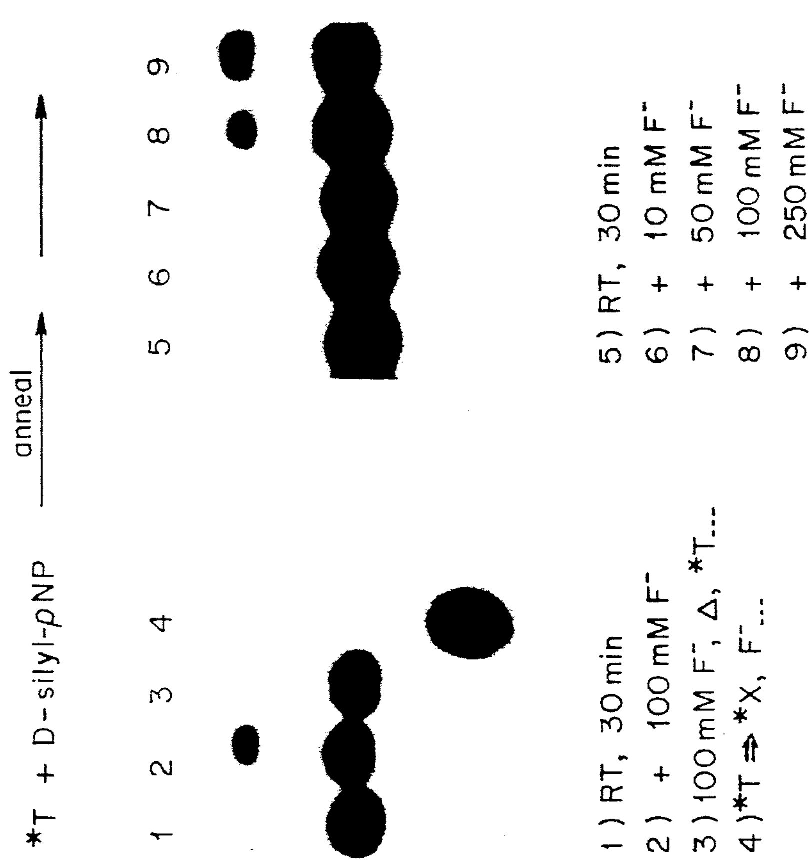
FIG. 3 is an autoradiogram of a 20% polyacrylamide gel further illustrating the cross-linking of the present invention, as discussed in Example 2.

FIG. 3 shows another autoradiogram of a 20% polyacrylamide gel. *T is the target strand and D-silyl-pNP is Compound 1.7a-L-Pr. The concentrations, quenching and analyses are all the same as described above for FIG. 1. Reactions were carried out at room temperature for 30 minutes. Lane 1 indicates that no alkylation of the target (crosslinking) occurred in the absence of fluoride; lane two is the positive control demonstrating that the crosslinking was triggered by the presence of 100 mM fluoride; lane 3 shows that the reagent can be neutralized by treatment with 100 mM fluoride (40° C., 30 minutes) before *T is added. Lane 4 proves that our oligonucleotide reagent is specific for complementary sequences. A noncomplementary [$^{32}$P] labelled oligonucleotide (X) 14 nucleotides long ([$^{32}$P]-5'-CATGCGTTCCCGTG SEQ ID NO:2) did not react with Compound 1.7a-L-Pr after addition of 100 mM fluoride. For the samples in lanes 5–9, the fluoride concentration was varied from 0.0–250 mM.

Figure 4:
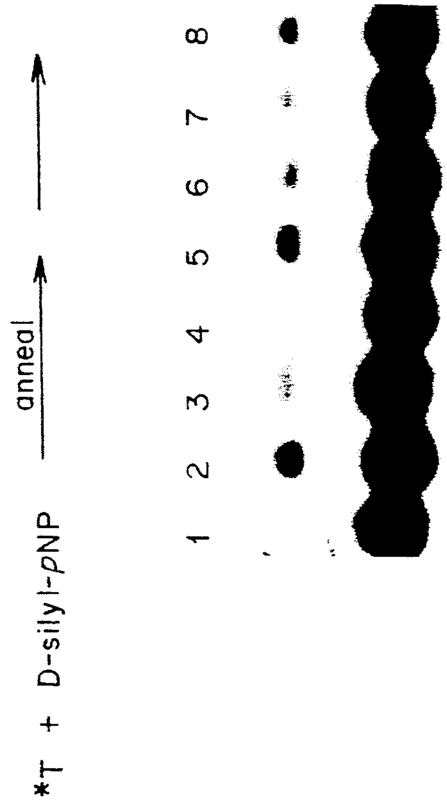
FIG. 4 is an autoradiogram showing that fluoride is not the only possible ionic triggering agent, as discussed in Example 2.

FIG. 4 shows that fluoride is not the only possible triggering agent. The signal for inducing reaction is not so much dependent on fluoride as it is dependent on a general increase in ionic strength. Accordingly, silyl containing reactive centers can be used for both in vivo and in vitro uses. No other ionic strength dependant covalent binding reagent has ever before been proposed or tested.

Protocol 1.4: Synthesis of reactive centers with reactivity similar to Compound 1.7a-c.

By treating Compound 1.6 with various nucleophiles (X), a series of related appendages for triggered reaction were produced.

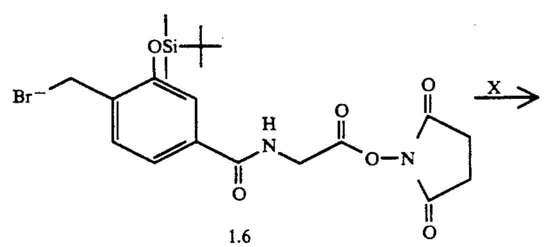

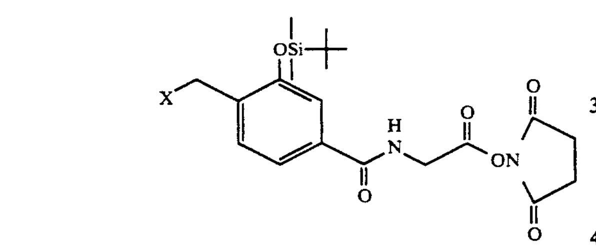

EXAMPLE 3

Reactive centers other than those represented by 1.7 have been constructed for inducible and selective cross-linking of the complex formed by a probe (L-Pr) and target (T).

SCHEME 2

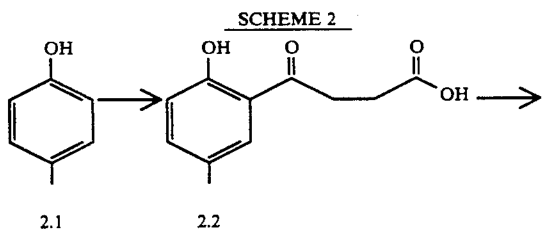

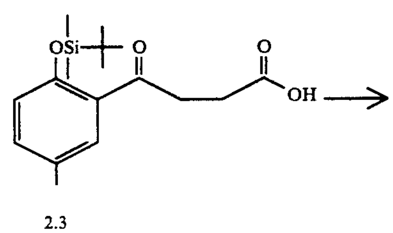

-continued
SCHEME 2

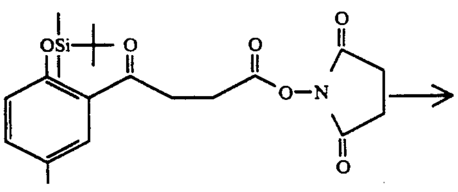

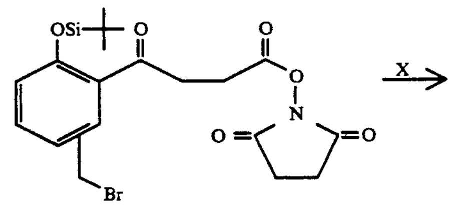

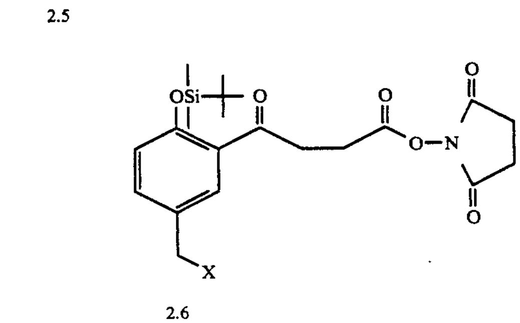

Protocol for the preparation of a reactive center designed for coupling to an aminolinker probe (L-Pr)

3-(5-methylbenzoyl)propionic acid (Compound 2.2). As shown in Scheme 2 Compound 2.2 was prepared by the method of Raval et al., *J. Univ. Bombay,* 7, Pt. 3, 184 (1983); CA 33, 3779 (1989). p-Cresol (4.0 g, 37 mmol) and succinic anhydride (3.4 g, 34 mmol) were combined in 1,1,2,2-tetrachloroethane (40 mL) and the mixture was heated to 60° C. Aluminum chloride (9.5 g, 71 mmol) was then added to the solution at a rate of 2 g/20 min. Once this was complete the reaction was heated to 135° C. for 30 min. After cooling, water and ether (30 mL of each) were added and the aqueous layer was extracted with 3×20 mL of ether. The combined organic fractions were dried and the remaining residue was purified by flash silica chromatography to yield 2.2 g (28.5%). $^1$HNMR δ 7.62 (s, 1H), 7.30 (d, 1H), 6.85 (d, 1H), 3.32 (t, 2H), 2.35 (t, 2H), 2.22 (s, 1H).

3-(2-t-Butyldimethysiloxy-5-methylbenzoyl) propionic acid (Compound 2.3). t-Butyldimethylsilyl chloride (2.3 g, 18.6 mmol) was added to a solution of Compound 2.2 (1.0 g, 18.6 mmol), triethylamine (0.9 g, 8.9 mmol) and THF (15 ml) at room temperature. The reaction mixture was then stirred for three hours at 40° C. The triethylammonium chloride was precipitated and removed after addition of 10 mL ethyl acetate:hexanes (3:1). The filtrate was separated by flash silica chromatography to yield a yellow liquid (1.45 g). This material was consistent with a disilyl derivative of 2.2 and could be used directly to form the desired product. For example, an ether solution (20 mL) of this liquid (0.5 g, 1.1 mmol) was treated with two drops of water and stirred overnight at room temperature. After the solvent was removed, the product was purified on flash silica chromatography to yield a white solid (0.3 g, 81%). $^1$H-NMR δ 7.30 (s, 1H), 7.02 (d, 1H), 6.66 (d, 1H), 3.22 (t, 2H), 2.26 (t, 2H), 2.18 (s, 3H), 0.85 (s, 9H), 0.14 (s, 6 H).

3-(2-t-Butyldimethylsiloxyl-5-methylbenzoyl) propionic acid N-hydroxysuccinimide ester (Compound 2.4). Hydroxysuccinimide (0.064 g, 0.31 mmol) was added to a solution of Compound 2.3 (0.1 g, 0.31 mmol) in DMF (3 ml). After was added. The reaction mixture was stirred for three hours at 4° C. and then filtered to remove the dicyclohexylurea. The filtrate was washed with water, dried and evaporated. The remaining residue was separated by flash silica chromatography to yield a white solid (0.096 g, 74%). $^1$H-NMR δ 7.14 (s, 1H), 7.11 (d, 1H), 6.73° (d, 1H), 3.37 (t, 2H), 2.93 (t, 2H), 2.77 (s, 4H), 2.22 (s, 3H), 0.92 (s, 9H), 0.21 (s, 6H).

3-(2-t-Butyldimethylsiloxyl-5-(bromomethyl)benzoyl) propionic acid N-hydroxysuccinimide ester (Compound 2.5). NBS (0.067 g, 0.37 mmol) and Compound 2.4 (0.13 g, 0.31 mmol) were combined in $CCl_4$ (3 ml). This solution was then maintained at 20° C. and irradiated with a 275 W sunlamp (Sears, #34-105) for fifteen minutes. After the solid succinimide was filtered away, the filtrate was evaporated. The residue remaining was purified by flash silica chromatography to yield a yellow solid (0.072 g, 45%). $^1$H-NMR δ 7.65 (s, 1H), 7.36 (d, 1H), 6.78 (d, 1H), 4.39 (s, 2H), 3.37 (t, 2H), 2.98 (t, 2H), 2.76 (s, 4H), 0.94 (s, 9H), 0.30 (s, 6H).

3-(2-t-Butyldimethylsiloxyl-5-(chloromethyl)benzoyl) propionic acid N-hydroxysuccinimide ester (Compound 2.6a). Potassium chloride (0.68 g, 0.15 mmol) was added to a solution of 2.5 (0.05 g, 0.1 mmol) in acetonitrile (5 ml). The reaction mixture was stirred for two hours at 40° C. and then washed. The organic phase was dried, evaporated and separated by flash silica chromatography to yield a white solid (0.034 g, 72%). $^1$H-NMR δ 7.65 (s, 1H), 7.32 (d, 1H), 6.81 (d, 1H), 4.48 (s, 2H), 3.36 (t, 2H), 2.96 (t, 2H), 2.77 (s, 4H), 0.93 (s, 9H), 0.24 (s, 6H).

Each of these silyloxy aromatic aromatic alkylating agents can be substituted by replacing the bromo with the other X groups, such as acetate, p-nitroplenolate and the like, as described in Example 2.

EXAMPLE 4

In a generalized embodiment, the silyloxy substituent may be in direct conjugation with the —CHX— group (for example, orth or para when attached to a phenyl ring) and an appendage for joining the aromatic system to the linker-probe (L-Pr) may be designed in any known manner. However, not all combinations were found to be appropriate due to the intrinsic reactivity of specific arrangement of functional groups.

SCHEME 3

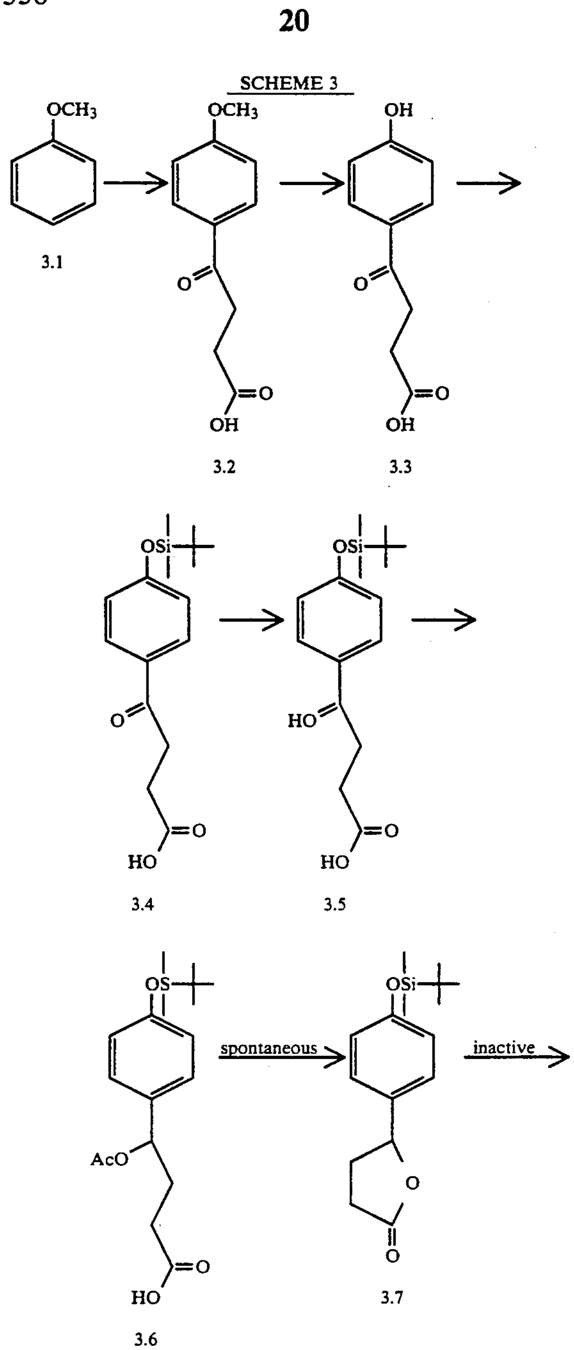

3-(4-methoxylbenzoyl)propionic acid (Compound 3.2). As illustrated in Scheme 3, a solution of p-anisole (4.32 g, 50 mmol) and succinic anhydride (4.14 g, 40 mmol) were combined in 1,1,2,2-tetrachloroethane (10 mL) and nitrobenzene (40 mL) at 4° C. Aluminum chloride (24.56 g, 180 mmol) was then added gradually. The temperature was kept at 0°-5° C. and stirred overnight. Water was added and neutralized to quench the reaction. The aqueous phase was separated and washed with ether then reacidified and washed with ether again. The ether fractions were combined, dried and evaporated. The remaining residue was purified by flash silica chromatography to yield a white solid (7.55 g, 88%). $^1$H-NMR ($CDCl_3$) δ 7.98 (d, 3H), 6.88 (d, 2H), 3.76 (s, 3H), 3.30 (t, 2H), 2.76 (t, 2H).

3-(4-Hydroxylbenzoyl)propionic acid (Compound 3.3). The methoxy derivative 3.2 (14.54 g, 70 mmol) was dissolved in iodine free hydriodic acid (150 mL) and refluxed at 140° C. for four hours. After the resulting brown solution was cooled to room temperature, water was added and the mixture was neutralized. The aqueous phase was then washed with ether; the organic layers were combined, decolorized, dried and evaporated. The remaining residue was purified by flash silica chromatography to yield a white solid (11.93 g, 88%). $^1$H NMR ($CDCl_3$) δ 8.20 (d, 2H), 7.02 (d, 2H), 3.32 (t, 2H), 2.88 (d, 2H).

3-(4-(t-Butyldimethylsiloxyl)benzoyl)propanoic acid (Compound 3.4). t-Butyldimethylsilyl chloride (0.63 g, 4 mmol) was added a solution of Compound 3.3 (0.23 g, mol), triethylamine (0.21 g, 20 mmol) and THF (20 mL); this was kept stirred at room temperature for 3 hours. Solvent was then evaporated and the residue was dissolved in ether, washed with dilute HCl and then by saturated bicarbonate. The organic phase was dried and evaporated to yield the disilyl derivative of Compound 3.3. This material could be purified by flash silica chromatography (0.36 g, 78%) and stored, or it could be used immediately. The disilyl compound (0.36 g, 4 mmol) was dissolved in 2-propanol (10 mL) and stirred overnight at room temperature. The solvent was removed by evaporation and replaced with ether. This mixture was then washed with water, dried, evaporated and separated on flash silica chromatography to yield a white solid (0.23 g, 82%). $^1$H NMR ($CDCl_3$) δ 7.88 (d, 2H), 6.86 (d, 2H), 3.26 (t, 2H), 2.76 (t, 2H), 0.98 (s, 9H), 0.86 (s, 6H).

4-(4-t-Butyldimethylsiloxyl)phenyl-4-hydroxybutyric acid (Compound 3.5). A mixture of Compound 3.4 (0.55 g, 2 mmol), $NaBH_4$ (0.04 g, 1 mmol) and methanol (5 mL) was heated to 50.C. After 10 hours, the resulting solid was removed by filtration and the solution was evaporated to dryness. The remaining residue was purified on flash silica chromatography to yield a white solid (0.31 g, 56%). $^1$H NMR ($CDCl_3$) δ 7.17 (d, 2H), 6.76 (d, 2H), 4.67 (t, 1H), 2.48 (t, 2H), 2.07 (m, 2H), 0.98 (s, 9H), 0.10 (s, 6H).

4-(t-Butyldimethylsiloxyl)phenyl)-4-acetoxybutyric acid (Compound 3.6) (X=acetate). Acetic anhydride (0.13 g, 1 mmol), triethylamine (0.13 g, 1.2 mmol) and Compound 3.5 (0.22 g, 0.6 mmol) were mixed in $CHCl_3$ for 5 hours at room temperature. The solution was then washed with sodium bicarbonate, dilute HCl and finally dried and evaporated. The remaining residue was purified on flash silica chromatography to yield a solid (0.15 g, 61%). $^1$H NMR ($CDCl_3$) δ 7.06 (d, 2H), 6.60 (d, 2H), 5.26 (m, 1H), 2.43 (m, 3H), 2.05 (q, 2H), 0.86 (s, 9H), −0.12 (s, 6H).

Using related chemical techniques derivatives were made in which X=Br (Compound 3.7) internal cyclization prevented further development of this specific approach.

EXAMPLE 5

In order to produce an alkylating agent that is selectively generated in the presence of an ionic strength modifying agent (MX), such as potassium fluoride, the reactive appendage should include a silyloxy group. Related derivatives containing a silyl substitution at a benzyl position are believed to be too stable for the applications described for this invention. Specifically, the characteristics of the —O—Si(R)$_3$ bond but not a —(R)$_2$C—Si(R')$_3$ are optimal for the controlled alkylation of a target. For example:

SCHEME 4

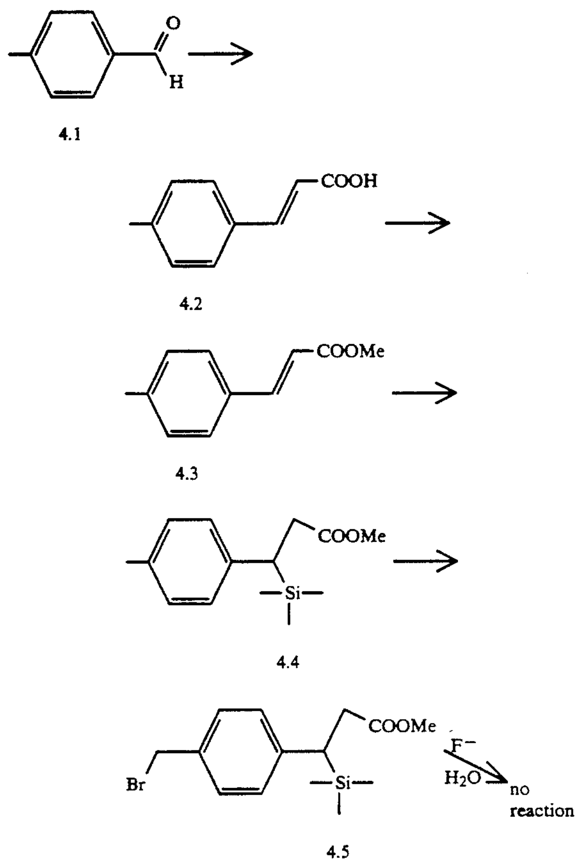

These compounds were synthesized and characterized. Compound 4.5 was found to be too stable for use in an aqueous system.

Thus, while we have described what are presently the preferred embodiments of the present invention, other and further changes and modifications could be made thereto without departing from the scope of the invention, and it is intended by the inventors herein to claim all such changes and modifications.

SEQUENCE LISTING ( 1 ) GENERAL INFORMATION ( i i i ) NUMBER OF SEQUENCES: 3

( 2 ) INFORMATION FOR SEQUENCE ID NO:1:

( i ) SEQUENCE CHARACTERISTICS:

-continued ( A ) LENGTH: 15 Nucleotides
( B ) TYPE: Nucleic Acid
( C ) STRANDEDNESS: Single
( D ) TOPOLOGY: Linear ( i i ) MOLECULE TYPE: Synthetic DNA ( i i i ) HYPOTHETICAL: No ( i v ) ANTI- SENSE: No ( v i i ) IMMEDIATE SOURCE: Synthesized ( x i ) SEQUENCE DESCRIPTION:SEQ ID NO:1

ACGTCAGGTG GCACT 15

( 2 ) INFORMATION FOR SEQUENCE ID NO:2:

( i ) SEQUENCE CHARACTERISTICS:
( A ) LENGTH: 20 Nucleotides
( B ) TYPE: Nucleic Acid
( C ) STRANDEDNESS: Single
( D ) TOPOLOGY: Liniar ( i i ) MOLECULE TYPE: Synthetic DNA ( i i i ) HYPOTHETICAL: No ( i v ) ANTI- SENSE: No ( v i ) ORIGINAL SOURCE: Synthesized ( x i ) SEQUENCE DESCRIPTION:SEQ ID NO:2:

AGTGCCACCT GACGTCTAAG 20

( 2 ) INFORMATION FOR SEQUENCE ID NO:3:

( i ) SEQUENCE CHARACTERISTICS:
( A ) LENGTH: 14 Nucleotides
( B ) TYPE: Nucleic Acid
( C ) STRANDEDNESS: Single
( D ) TOPOLOGY: Linear ( i i ) MOLECULE TYPE: Synthetic DNA ( i i i ) HYPOTHETICAL: No ( i v ) ANTI- SENSE: No ( v i ) ORIGINAL SOURCE: Synthesized ( x i ) SEQUENCE DESCRIPTION:SEQ ID NO:2:

CATGCGTTCC CGTG 14

We claim:

1. A silyloxy aromatic probe having the formula:

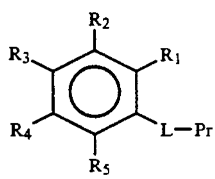

wherein when $R_1$=—OSi($R_6R_7R_8$), then $R_2$ and/or $R_4$ is==—$CHR_9X$;

when $R_2$=—OSi($R_6R_7R_8$), then $R_1$, $R_3$ and/or $R_5$ is=—$CHR_9X$;

when $R_3$=—OSi($R_6R_7R_8$), then $R_2$ and/or $R_4$ is==—$CHR_9X$;

when $R_4$=—OSi($R_6R_7R_8$), then $R_1$, $R_3$ and/or $R_5$ is=—$CHR_9X$;

when $R^5$=—Osi($R_6R_7R_8$), then $R_2$ and/or $R_4$ is==—$CHR_9X$;

wherein said $R_6$, $R_7$, $R_8$=various alkyl or aromatic groups;

X leaving group; wherein said $R_9$, is H, or an organic compound, such as an aliphatic or alkyl group L is a linking group for attachment to a probe which may be positioned at any carbon atom of the ring; and Pr is a probe for binding to a target molecule.

2. A silyloxy aromatic probe according to claim 1, wherein said silyloxyl aromatic probe alkylates a target molecule after ionic activation; and wherein X is selected from the group consisting of Cl, F, I, OCOR, OH, $OSO_2CH_3$, $OSO_2C_6H_4CH_3$-p, OR, OCONHR, $OCONHCH_2CH_2R$, Br, phenol, nitro-phenol and thio-phenol.

3. A silyloxy aromatic probe according to claim 2, wherein L comprises a chain —$R_{10}$—$R_{11}$—$R_{12}$—, in which $R_{10}$ is selected from the group consisting of NH, S, O and $CH_2$, in which $R_{11}$ comprises a stable spacer group between $R_{11}$ and $R_{12}$, and in which $R_{12}$ is selected from the group consisting of $NH_2$, SH, OH and COOH; and wherein Pr is a probe that includes a localizing moiety, such as an oligonucleotide that preferentially localizes to an DNA or RNA.

4. A silyloxy aromatic probe according to claim 3 wherein $R_6$, $R_7$ and $R_8$ comprises a t-butyl moiety.

5. A silyloxy aromatic probe according to claim 3, wherein Pr is an oligonucleotide.

6. A silyloxy aromatic probe according to claim 5, wherein Pr is a DNA strand.

7. A silyloxy aromatic probe according to claim 5, wherein said oligonucleotide is linked to L by its 5' terminus.

8. A silyloxy aromatic probe according to claim 5, wherein the oligonucleotide is linked to L by its 3' terminus.

9. A silyloxy aromatic probe according to claim 5, further comprising a modified base on said oligonucleotide suitable for linking to $R_{12}$ at said modified base.

10. A silyloxy aromatic probe according to claim 5, further comprising a modified phosphoribose backbone on said oligonucleotide suitable for linking to $R_{12}$ at said modified phosphodeoxyribose backbone.

11. A silyloxy aromatic probe composition having the formula:

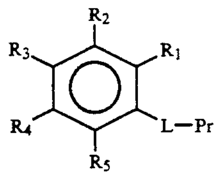

wherein $R_2$=—$OSi(R_6R_7R_8)$, $R_3$=—$CH_2X$; said $R_6$, $R_7$, $R_8$=various alkyl or aromatic groups; X=leaving group; L is a linking group for to a probe which may be positioned at any carbon atom of the ring; and P is a probe for binding to a target molecule.

12. A silyloxy aromatic probe according to claim 11, wherein L comprises a chain —$R_{10}$—$R_{11}$—$R_{12}$—, in which $R_{10}$ is selected from the group consisting of N, S, O and $CH_2$, in which $R_{11}$ comprises a stable spacer group between $R_{10}$ and $R_{11}$, and in which $R_{12}$ is selected from the group consisting of $NH_2$, SH, OH and COOH; and wherein Pr is a probe that includes a localizing moiety, such as an oligonucleotide DNA or RNA.

13. A silyloxy aromatic probe according to claim 12, wherein $R_6$, $R_7$ and $R_8$ comprises a t-butyl moiety.

14. A silyloxy aromatic probe according to claim 12, wherein Pr is an oligonucleotide.

15. A silyloxy aromatic probe according to claim 12, wherein Pr is a DNA strand.

16. A silyloxy aromatic probe according to claim 14, wherein said oligonucleotide is linked to L by its 5' terminus.

17. A silyloxy aromatic probe according to claim 14, wherein said oligonucleotide is linked to L by its 3' terminus.

18. A silyloxy aromatic probe according to claim 14, further comprising a modified base on said oligonucleotide suitable for linking to $R_{12}$ at said modified base.

19. A silyloxy aromatic probe according to claim 14, further comprising a modified phosphoribose backbone on said oligonucleotide suitable for linking to $R_{12}$ at said modified phosphoribose backbone.

20. A silyloxy aromatic probe recited in claim 13, wherein X comprises $C_6H_4NO_3$.

21. A process for selectively alkylating a target molecule, comprising steps of:

a) providing a probe for recognizing a predetermined binding site on a target molecule;
b) providing a silyloxy aromatic derivative for linking to the probe;
c) linking the probe to the silyloxy aromatic derivative to form a targeted alkylating agent;
d) introducing the targeted alkylating agent to a system containing a target molecule, whereby the probe associates with the target molecule, localizing the linked silyloxy aromatic derivative near the target molecule; and
e) activating the targeted alkylating agent, thereby causing covalent binding between the linked aromatic derivative proximal to the association site of the probe with the target molecule.

22. A process as recited in claim 21, wherein the targeted alkylating agent has the molecular formula:

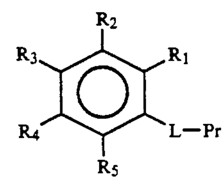

wherein when $R_1$=—$OSi(R_6R_7R_8)$, then $R_2$ and/or $R_4$ is=—$CHR_9X$;

when $R_2$=—$OSi(R_6R_7R_8)$, then $R_1$, $R_3$ and/or $R_5$ is=—$CHR_9X$;

when $R_3$=—$OSi(R_6R_7R_8)$, then $R_2$ and/or $R_4$ is=—$CHR_9X$;

when $R_4$=—$OSi(R_6R_7R_8)$, then $R_1$, $R_3$ and/or $R_5$ is=—$CHR_9X$;

when $R_5$=—$OSi(R_6R_7R_8)$, then $R_2$ and/or $R_4$ is=—$CHR_9X$;

wherein said $R_6$, $R_7$, $R_8$=various alkyl or aromatic groups; said $R_9$ is H, or an organic group, such as an aliphatic oralkyl group X=leaving group; L is a linking group for attachment to a probe which may be positioned at any carbon atom of the ring; and Pr is a probe for binding to a target molecule.

23. A process as recited in claim 22, wherein said linking step (c) further comprises adapting the silyloxy aromatic derivative by the addition of an acidic linking group suitably modified for linking the silyloxy aromatic derivative to the probe molecule.

24. A process as recited in claim 23, wherein said probe is an oligonucleotide, and further comprising the step of:

suitably modifying a base of said oligonucleotide probe for linking to L at the modified base.

25. A process as recited in claim 23, wherein said probe is an oligonucleotide, and further comprising the step of:

suitably modifying a phosphoribose backbone of said oligonucleotide probe for linking to L at the modified phosphoribose backbone.

26. A process as recited in claim 23, wherein said activating step comprises introduction of an ionic activating signal.

27. A process as recited in claim 23, wherein said adapting step further includes brominating the X group, and said activating step comprises activation with an ionic signal.

28. A process recited in claim 27, wherein said brominating step is followed by substituting the bromine by molecules selected from the group consisting of Cl, F, $OCONHCH_2CH_2R$, Br, phenol, nitro-phenol and thiophenol.

29. A process as recited in claim 28, wherein L comprises a chain —$R_{10}$—$R_{11}$—$R_{12}$—, in which $R_{10}$ is selected from the group consisting of N, S, O and $CH_2$, in which $R_{11}$ comprises a stable spacer group between $R_{10}$ and $R_{12}$, and in which $R_{12}$ is selected from the group consisting of $NH_2$, SH, OH and COOH; and wherein Pr is a probe that includes a localizing moiety, such as an oligonucleotide that preferentially localizes to.

30. A process as recited in claim 28, wherein said process is carried out in vitro.

* * * * *

UNITED STATES PATENT AND TRADEMARK OFFICE
CERTIFICATE OF CORRECTION

PATENT NO. : 5,296,350

DATED : March 22, 1994

INVENTOR(S) : Rokita, et al.

It is certified that error appears in the above-indentified patent and that said Letters Patent is hereby corrected as shown below:

IN THE ABSTRACT

Line 14, now reads "ionic signal, (X)", should read --ionic signal (X)--.

Column 1, Line 24 now reads "et al., 37 DNA", should read --et al., DNA--.

Column 2, Line 53 now reads "(1986); nd Meyer", should read --(1986); and Meyer--.

Column 6, Line 8 now reads "$-OC_6H_4HO_2$(nitro-", should read -- $-OC_6H_4NO_2$(nitro- --.

Column 7, Line 68 now reads "probe examples", should read --probe Pr, examples--.

CERTIFICATE OF CORRECTION

PATENT NO. : 5,296,350

DATED : March 22, 1994

INVENTOR(S) : Rokita, et al

It is certified that error appears in the above-indentified patent and that said Letters Patent is hereby corrected as shown below:

Columns 9-12 now reads

SCHEME A

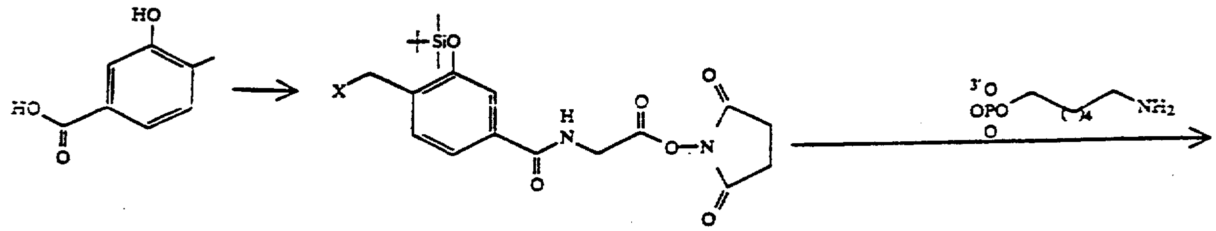

should read

SCHEME A

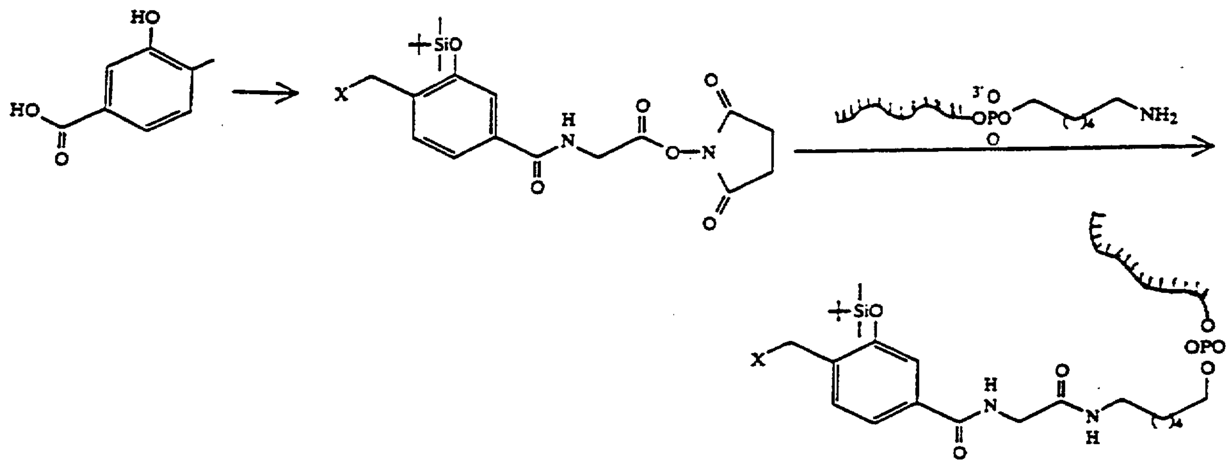

UNITED STATES PATENT AND TRADEMARK OFFICE
CERTIFICATE OF CORRECTION

PATENT NO. : 5,296,350

DATED : March 22, 1994

INVENTOR(S) : Rokita, et al

It is certified that error appears in the above-indentified patent and that said Letters Patent is hereby corrected as shown below:

Column 11, Line 31-65

Now Reads:

Should Read:

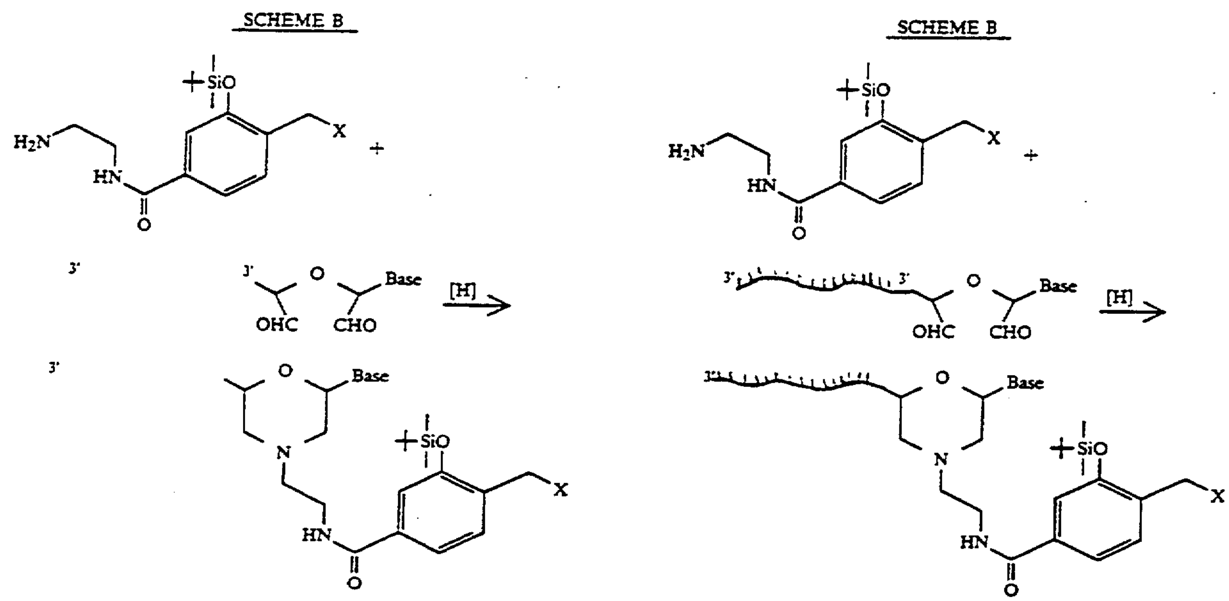

UNITED STATES PATENT AND TRADEMARK OFFICE

CERTIFICATE OF CORRECTION

PATENT NO. : 5,296,350

DATED : March 22, 1994

INVENTOR(S) : Rokita, et al.

It is certified that error appears in the above-indentified patent and that said Letters Patent is hereby corrected as shown below:

| | |
|---|---|
| Column 14, Line 12 | now reads "(81.5%) of-a", should read --(81.5%) of a--; |
| Column 14, Line 15 | now reads "3+- Butyldimethy Isiloxyl", should read --3-t-Butyldimethylsiloxyl--. |
| Column 14, Line 20 | now reads "4C.", should read --4°C.--; |
| Column 14, Line 49 & 50 | now reads "LRMS m/Z", should read --LRMS m/z--; |
| Column 15, Line 26 | now reads "within the of those", should read --within the knowledge of those--. |
| Column 15, Line 32 | now reads "Oligonucleotide linker", should read, --Oligonucleotide-linker--. |

UNITED STATES PATENT AND TRADEMARK OFFICE

CERTIFICATE OF CORRECTION

PATENT NO. : 5,296,350

DATED : March 22, 1994

INVENTOR(S) : Rokita, et al.

It is certified that error appears in the above-indentified patent and that said Letters Patent is hereby corrected as shown below:

Column 16, Line 6 — now reads "AV260)", should read --$AV_{260}$)--;

Column 16, Line 11 — now reads "SEQ ID No: 1", should read --SEQ ID NO: 2--;

Column 16, Line 23 — now reads "than 1o min", should read --than 10 min--.

Column 19, Line 11 — now reads "Hydroxysuccinimide", should read --N-Hyroxysuccinimide--.

Column 19, Line 14 — now reads "After was added", should read -- After this mixture was cooled to 4°C, DCC (0.036 g, 0.31 mmol) was added.

UNITED STATES PATENT AND TRADEMARK OFFICE

CERTIFICATE OF CORRECTION

PATENT NO. : 5,296,350

DATED : March 22, 1994

INVENTOR(S) : Rokita, et al.

It is certified that error appears in the above-indentified patent and that said Letters Patent is hereby corrected as shown below:

Column 19, Line 21 now reads "6.73°" should read --6.73--.

Column 19, Line 30, now reads "Sears, #34-105)", should read --(Sears #34-7105--.

Column 20, Line 19-34, now reads:

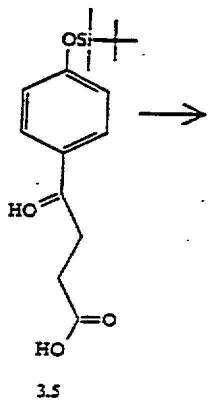

should read:

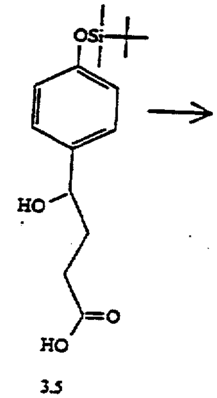

UNITED STATES PATENT AND TRADEMARK OFFICE
CERTIFICATE OF CORRECTION

PATENT NO. : 5,296,350

DATED : March 22, 1994

INVENTOR(S) : Rokita, et al

It is certified that error appears in the above-indentified patent and that said Letters Patent is hereby corrected as shown below:

Column 21, Line 34 now reads "50.C", should read --50°C--.

Column 23, SEQ. ID NO: 2 now reads "Liniar", should read --Linear--.

IN THE CLAIMS:

Column 24, Line 48, now reads"$R^5$=-Osi($R_6R_7R_8$)", should read --$R_5$=-OSi($R_6R_7R_8$)--.

Column 25, Line 38, now reads "for to a probe", should read --for attachment to a probe--.

Column 26, Line 44, now reads "oralkyl group", should read --or alkyl group--.

UNITED STATES PATENT AND TRADEMARK OFFICE
CERTIFICATE OF CORRECTION

PATENT NO. : 5,296,350

DATED : March 22, 1994

INVENTOR(S) : Rokita, et al

It is certified that error appears in the above-indentified patent and that said Letters Patent is hereby corrected as shown below:

Column 27, Line 5, now reads "consisting of Cl, F, $OCONHCH_2CH_2R$", should read --consisting of Cl, F, I, OCOR, OH, $OSO_2CH_3$, $OSO_2C_6H_4CH_3$-p, OR, OCONHR,--.

Signed and Sealed this

Thirteenth Day of June, 1995

Attest:

BRUCE LEHMAN

*Attesting Officer*

*Commissioner of Patents and Trademarks*